United States Patent [19]

Selva et al.

[11] Patent Number: 5,202,241
[45] Date of Patent: Apr. 13, 1993

[54] ANTIBIOTIC GE 2270

[75] Inventors: Enrico Selva, Via Di Vittorio; Nicoletta Montanini, Via Capuana; Graziella Beretta, Via Belgirate; Beth P. Goldstein, Corso Garibaldi; Maurizio Denaro, Sporting Mirasole, all of Italy

[73] Assignee: Gruppo Lepetit S.p.A., Milan, Italy

[21] Appl. No.: 713,567

[22] Filed: Jun. 11, 1991

Related U.S. Application Data

[62] Division of Ser. No. 401,278, Aug. 31, 1989, abandoned.

[30] Foreign Application Priority Data

Sep. 9, 1988 [GB] United Kingdom ............... 8821160

[51] Int. Cl.$^5$ ............................................. C12P 21/04
[52] U.S. Cl. ...................................... 435/71.3; 435/41
[58] Field of Search ................................. 435/41, 71.3

[56] References Cited

PUBLICATIONS

CA 89(25):210992p 1978.

*Primary Examiner*—Paul J. Killos
*Attorney, Agent, or Firm*—J. Michael Dixon

[57] ABSTRACT

The present invention is directed to a new antibiotic substance denominated antibiotic GE 2270, the addition salts thereof, the pharmaceutical compositions thereof and their use as medicaments, particularly in the treatment of infectious diseases involving microorganisms susceptible to them.

2 Claims, 4 Drawing Sheets

ANTIBIOTIC GE 2270

CROSS-REFERENCE TO RELATED APPLICATION

This is a divisional of application Ser. No. 401,278, filed Aug. 31, 1989, now abandoned.

The present invention is directed to a new antibiotic substance denominated antibiotic GE 2270, the addition salts thereof, the pharmaceutical compositions thereof and their use as medicaments, particularly in the treatment of infectious diseases involving microorganisms susceptible to them.

The compounds of the invention are also active as growth promotant agents in animals, such as poultry, swine, ruminants, etc.

Another object of the invention is a process for preparing antibiotic GE 2270 which includes culturing *Planobispora rosea* ATCC 53773 or an antibiotic GE 2270 producing variant or mutant thereof and isolating the antibiotic of the invention from the mycelium and/or the fermentation broths.

*Planobispora rosea* ATCC 53773 was isolated from a soil sample and deposited on Jun. 14, 1988 with the American Type Culture Collection (ATCC), 12301 Parklawn Drive, Rockville, Md. 20852 Maryland, U.S.A., under the provisions of the Budapest Treaty.

The strain has been accorded accession number ATCC 53773.

The production of antibiotic GE 2270 is achieved by cultivating a *Planobispora* strain capable of producing it, i.e. *Planobispora rosea* ATCC 53773 or an antibiotic GE 2270 producing variant or mutant thereof, under aerobic conditions in an aqueous nutrient medium containing assimilable sources of carbon, nitrogen, and inorganic salts. Many of the nutrient media usually employed in the fermentation art can be used, however certain media are preferred. Preferred carbon sources are glucose, mannose, galactose, starch, corn meal and the like. Preferred nitrogen sources are ammonia, nitrates, soybean meal, peptone, meat extract, yeast extract, tryptone, aminoacids, and the like. Among the inorganic salts which can be incorporated in the culture media there are the customary soluble salts capable of yielding sodium, potassium, iron, zinc, cobalt, magnesium, calcium, ammonium, chloride, carbonate sulfate, phosphate, nitrate and the like ions.

Ordinarily, the antibiotic-producing strain is pre-cultured in a shake flask, then the culture is used to inoculate jar fermentors for production of substantial quantities of the antibiotic substances. The medium used for the pre-culture can be the same as that employed for larger fermentations, but other media can also be employed. The antibiotic GE 2270 producing-strain can be grown at temperatures between 20 and 40° C., preferably between 24° and 35° C.

During fermentation, the antibiotic production can be monitored by testing broth or mycelial extract samples for antibiotic activity for instance by bio-assays or TLC or HPLC procedures.

Sensitive organisms to antibiotic GE 2270 such as *Bacillus subtilis* and *S. aureus* can be used as test organisms. The bioassay is conveniently performed by the agar diffusion method on agar plates. Maximum production of antibiotic activity generally occurs between the second and the fifth day of fermentation.

Antibiotic GE 2270 is produced by cultivating the strain *Planobispora rosea* ATCC 53773, or an antibiotic GE 2270 producing mutant or variant thereof, and is mainly found in the mycelium.

In the present disclosure when dealing with the compounds of the invention in relation to their physico-chemical or biological properties, the term "antibiotic GE 2270" is generally considered to refer to antibiotic GE 2270 complex as recovered at the end of the fermentation process (see Example 2) as well as to antibiotc GE 2270 factor A which is its main component.

Morphological characteristics of *Planobispora rosea* ATCC 53773

*Planobispora rosea* ATCC 53773 grows well on most standard media. The vegetative mycelium forms long and irregularly branched filaments (0.5 to 1.0 micrometer) penetrating the agar and forming a compact growth on its surface. The mycelium remains unfragmented whether grown in liquid or in solid media. Its color ranges from light coral to pink coral on most of the tested media. The aerial mycelium is formed of long, wavy and slender hyphae with few lateral branches and grows in the air essentially parallel to the agar surface. The aerial mycelium, when present, has a white-pink color. Sporangia are formed singly or in groups along the hyphae of the aerial mycelium and are about 6.0 to 8.0 micron long and 1.0 to 1.2 micron wide. They are attached to the hypha by a short sporangiophore (1.0 to 2.0 micrometer long). A longitudinal pair of fusiform straight spores (3.0 to 3.5×1.0 to 1.2 micrometer) are formed in each sporangium. In the sporangia, the spores are separated by a transverse septum. After release from the sporangial envelope, the spores become motile by means of peritrichous flagella.

Cultural characteristics of *Planobispora rosea* ATCC 53773

For the examination of the cultural characteristics, *Planobispora rosea* ATCC 53773, was cultivated on various standard media suggested by Shirling and Gottlieb (Shirling E. B. and Gottlieb D., 1966—Method for characterization of Streptomyces species—Int. J. Syst. Bacteriol, 16, 313–340) with the addition of several media recommended by Waksman (Waksman, S. A. 1961—The Actinomycetes—The Williams and Wilkins Co. Baltimore; Vol. 2, 328-334).

Color determination was made, when necessary, by the method of Maerz and Paul (Maerz A. and M. Rea Paul, 1950—A Dictionary of Color—2nd Edition McGraw-Hill Book Company Inc. New York).

The ability of the organism to utilize different carbon sources was investigated by the method described by Shirling and Gottlieb.

The cultural and physiological characteristics and the carbon sources utilization are reported in Tables I, II, III.

The readings in Table I have been taken after two weeks of incubation at 28° C.

TABLE I

| Cultural characteristics of strain *Planobispora rosea* ATCC 53773 | |
|---|---|
| Culture media | Morphological Characteristics |
| Oatmeal agar 6% | Abundant growth with smooth surface, coral pink (2-H-10) abundant production of light pink aerial mycelium (1-A-9). |
| ISP 2 (yeast extract malt agar) | Abundant growth with wrinkled surface, light pink (2-E-9), trace of light aerial mycelium. |
| ISP 3 | Moderate growth with smooth surface, |

TABLE I-continued

Cultural characteristics of strain *Planobispora rosea* ATCC 53773

| Culture media | Morphological Characteristics |
|---|---|
| (oatmeal agar 2%) | light pink (2-E-8), trace of pinkish white aerial mycelium. |
| ISP 4 (inorganic salts starch agar) | Moderate growth with smoth surface, coral pink (2-E-10). |
| ISP n 5 (glycerol asparagine agar) | Moderate growth with smooth and flat surface, light pink (2-A-9), abundant production of white aerial mycelium. |
| ISP 6 (peptone yeast extract iron agar) | Moderate growht, slightly wrinkled light coral pink (1-A-10). |
| ISP 7 (tyrosine agar) | Moderate growth with smooth and thin surface light pink (1-A-9), abundant formation of light pink (1-C-9) aerial mycelium. |
| Hichey and Tresner's agar | Abundant growth with thick and wrinkled surface light coral pink (1-A-10), moderate production of light pink aerial mycelium. |
| Czapek glucose agar | Very scarce growth with smooth and thin surface, moderate production of light pink aerial mycelium. |
| Glucose asparagine agar | Moderate growth with smooth and thin surface colorless, aerial mycelium absent. |
| Nutrient agar | Good growth with smooth surface light orange with a pinkish tinge (9-A-7). |
| Bennett's agar | Moderate growth with slightly wrinkled surface light amber pink (10-A-6). |
| Calcium malate agar | Poor growth with smooth and flat surface colorless. |
| Skim milk agar | Moderate growthwith smooth surface coral pink (2-F-9). |
| Egg albumin agar | Poor growth with smooth and thin surface colorless to light pink (2-A-8). |
| Dextrose tryptose agar | No growth |
| Potato agar | Good growth with smooth surface light orange with a pinkish tinge (9-A-7). |

Letter and numbers refer to the color determined according to Maerz and Paul (see above)

TABLE II

Physiological characteristics of *Planobispora rosea* ATCC 53773

| Tests | Results |
|---|---|
| Starch hydrolysis | positive |
| Hydrogen sulphide formation | negative |
| Tyrosine reaction | positive |
| Casein hydrolysis | weakly positive |
| Calcium malate digestion | negative |
| Gelatin liquefaction | weakly positive |
| Milk coagulation | negative |
| Milk peptonization | negative |
| Nitrate reduction | positive |

TABLE III

Carbohydrate utilization

| Carbon source | Growth |
|---|---|
| Arabinose | + |
| Xylose | + |
| Ribose | − |
| Fructose | +/− |
| Galactose | − |
| Glucose | + |
| Rhamnose | − |
| Lactose | − |
| Sucrose | − |
| Maltose | + |
| Raffinose | − |
| Cellulose | − |
| Mannitol | − |
| Salicin | + |

TABLE III-continued

Carbohydrate utilization

| Carbon source | Growth |
|---|---|
| Inositol | + |
| Cellobiose | − |

+ moderate growth
+/− scarce growth
− no growth

For this test medium No. 8 is employed and the results are evaluated after 2 weeks of incubation at 28°–30° C.

Sensitivity to temperature

The optimum growth temperature ranges from 28° C. to 37° C. No growth is observed at 15° C. and 50° C., moderate growth at 20° C.

Chemotaxonomical characteristics

Cell wall analysis:

The analysis of aminoacids present in the cell wall was carried out by the method described by Becker et al ("Rapid differentiation between Nocardia and Streptomyces by paper chromatography of whole cell hydrolyzated", Appl.Microbiol. 12, 421–423, 1964 ).

The analysis of the whole cell hydrolyzated revealed the presence of meso-diaminopimelic acid.

No glycine was found upon analysis of the pure cell wall preparation obtained according to the method of Kawamoto et al. (Kawamoto I., O. Tetsuo, and N. Takashi, "Cell wall composition of *Micromonospora olivoasterosporia*, *Micromonospora sagamiensis* and related organism." J. of Bacteriol. 146, 527–534, 1981).

Whole cell sugar pattern:

The analysis of the sugar content in the whole cell hydrolyzated was carried out by the method of Lechevalier M. P. ("Identification of aerobe actinomycetes of clinical importance" J. Lab. Clin. Med. 71, 934–944, 1968 ), using thin layer chromatography cellulose sheets as described by Staneck J. L. and G. D. Roberts ("Simplified approach to identification of aerobic actinomycetes by thin layer chromatography", Appl. Microbiol. 28, 226–231, 1974) with the following solvent system: Ethylacetate-Pyridine-Water (100:35:25 v/v).

The obtained results showed the presence of madurose (3-O-methyl-D-galactose) and absence of arabinose and galactose.

Identity of strain *Planobispora rosea* ATCC 53773

This strain was assigned to the genus *Planobispora* and classified as *Planobispora rosea* because of the following morphological and chemical characteristics:
a) The presence of meso-diaminopimelic acid and the absence of glycine in the cell wall (cell wall chemotype III)
b) The presence of madurose in the whole cell hydrolyzate (whole cell sugar pattern B)
c) The formation on the aerial mycelium of long and cylindrical sporangia containing a pair of motile spores
d) The pink color of the vegetative mycelium.

The morphological characteristics of *Planobispora rosea* ATCC 53773 reported above are not substantially different from those of a strain of *Planobispora rosea* which was described by J. E. Thieman et al in "The Actinomycetales", The Jena Intern. Symp. on Taxon., September 1968, ed. H. Prauser, Jena. It was deposited with the American Type Culture Collection were it received accession number 23866. No antibiotic production was described for this strain.

As with other microorganisms, the characteristics of the GE 2270 producing strains are subject to variation. For example, artificial variants and mutants of the strain can be obtained by treatment with various known mutagens, such as U.V. rays, X-rays, high frequency waves, radioactive rays, and chemicals such as nitrous acid, N-methyl-N'-nitro-N-nitrosoguanidine, and many others. All natural and artificial variants and mutants which belong to a species of the genus Planobispora and produce antibiotic GE 2270 are deemed equivalent to strain *Planobispora rosea* ATCC 53773 for the purposes of this invention and are contemplated to be within the scope of this invention.

As mentioned above, antibiotic GE 2270 is generally found mainly in the mycelium of the producing strain, while a minor amount of substance is found also in the fermentation broth.

The recovery of antibiotic GE 2270 from the mycelium or the fermentation broths of the producing microorganism is conducted according to known per se techniques such as extraction with solvents, precipitation by adding non-solvents or by changing the pH of the solution, partition chromatography, reverse-phase partition chromatography, ion-exchange chromatography, molecular exclusion chromatography and the like.

A preferred procedure for recovering the antibiotic substance of the invention from the mycelium includes extracting the filtered or centrifugated mycelium with a water-miscible organic solvent, concentrating the extracts and recovering the crude antibiotic substance by precipitation, optionally with the addition of a precipitating agent, by extraction of the aqueous residue with a water-immiscible organic solvent or by adsorption chromatography followed by elution of the desired product from the absorption matrix.

A preferred procedure for recovering the antibiotic substance of the invention from the fermentation broth, includes extraction with a water-immiscible organic solvent, followed by precipitation from the concentrated extracts possibly by adding a precipitating agent or further extraction of an aqueous residue thereof with a water-immiscible solvent. Alternatively, the fermentation broth can be contacted with an adsorption matrix followed by elution with a polar elution mixture. This chromatographic procedure can also be applied to a concentrated extract obtained from the fermentation broth instead of on the broth itself.

The term "water-miscible solvent" as used in this application, is intended to have the meaning currently given in the art to this term and refers to solvents that, at the conditions of use, are miscible with water in a reasonably wide concentration range.

Examples of water-miscible organic solvents that can be used in the extraction of the antibiotic substance of the invention from the mycelial mass are: lower alkanols, e.g. ($C_1$-$C_3$)alkanols such as methanol, ethanol and propanol; phenyl($C_1$-$C_3$)alkanols such as benzyl alcohol; lower ketones, e.g. ($C_3$-$C_4$)ketones such as acetone and ethylmethylketone; cyclic ethers such as dioxane and tetrahydrofurane; glycols and their products of partial etherification, such as ethylene glycol, propylene glycol and ethylene glycol monomethyl ether; lower amides such as dimethylformamide and diethylformamide.

The term "water-immiscible solvent" as used in this application, is intended to have the meaning currently given in the art to this term and refers to solvents that at the conditions of use are slightly miscible or practically immiscible with water in a reasonably wide concentration range, suitable for the intended use.

Examples of water-immiscible organic solvents that can be used in the extraction of the antibiotic substance of the invention from the fermentation broth are: the usual hydrocarbon solvents which may be linear, branched or cyclic such as hexane or cyclohexane; halogenated hydrocarbons such as chloroform, carbon tetrachloride, dichloroethane, fluorobromoethane, dibromoethane, trichloropropane, chlorotrifluorooctane and the like; aromatic hydrocarbons such as benzene, toluene, xylene and the like; esters of at least four carbon atoms, such as ethyl acetate, propyl acetate, ethyl butyrrate, and the like; alkanols of at least four carbon atoms which may be linear, branched or cyclic such as butanol, 1-pentanol, 2-pentanol, 3-pentanol, 1-hexanol, 2-hexanol, 3-hexanol, 3,3-dimethyl-1-butanol, 4-methyl-1-pentanol; 3-methyl-1-pentanol, 2,2-dimethyl-3-pentanol, 2,4-dimethyl-3-pentanol, 4,4-dimethyl-2-pentanol, 5-methyl-2-hexanol, 1-heptanol, 2-heptanol, 5-methyl-1-hexanol, 2-ethyl-1-hexanol, 2-methyl-3-hexanol, 1-octanol, 2-octanol, cyclopentanol, 2-cyclopentylethanol, 3-cyclopentyl-1-propanol, cyclohexanol, cycloheptanol, cyclooctanol, 2,3-dimethylcyclohexanol, 4-ethylcyclohexanol, cyclooctylmethanol, 6-methyl-5-hepten-2-ol, 1-nonanol, 2-nonanol, 1-decanol, 2-decanol and 3-decanol; straight or branched alkyl ethers and mixture thereof such as petroleum ether, ethyl ether, propyl ether, butyl ether, etc; and mixtures or functional derivatives thereof.

As known in the art, phase separation may be improved by salting.

When following an extraction an aqueous phase is recovered containing a substantial amount of an organic solvent, it may be convenient to azeotropically distill water from it. Generally, this requires adding a solvent capable of forming minimum azeotropic mixtures with water, followed by the addition of a precipitating agent to precipitate the desired product, if necessary. Representative examples of organic solvents capable of forming minimum azeotropic mixtures with water are n-butanol, benzene, toluene, butyl ether, carbon tetrachloride, chloroform, cyclohexane, 2,5-dimethylfurane, hexane and m-xylene; the preferred solvent being n-butanol.

Examples of precipitating agents are petroleum ether, lower alkyl ethers, such as ethyl ether, propyl ether and butyl ether, and lower alkyl ketones such as acetone.

Examples of chromatographic systems that can be conveniently used in the recovery of the antibiotic substance of the invention, are polystyrene or mixed polystyrene-divinylbenzene resins such as Amberlite XAD2 or XAD4 (Rohm and Haas), S112 (Dow Chemical Co.) and Diaion HP 20 (Mitsubishi); acrylic resins such as XAD7 or XAD8 (Rohm and Haas); polyamides such as polycaprolactames, nylons and cross-linked polyvinylpyrrolidones generally having a pore volume (ml/g) ranging between 1 and 5, surface area ($m^2$/g) ranging between 1 and 100, apparent density (g/ml) ranging between 0.15 and 0.50, average pore diameter (Ångstrom units) ranging between 100 and 3000 and particles size distribution where at least 40 percent of the particle size is lower than 300 micrometers, such as Polyamide-CC 6, Polyamide-SC 6, Polyamide-CC 6.6, Polyamide-CC 6AC and Polyamide-SC 6AC (Macherey-Nagel & Co., West Germany), the polyvinylpyrrolidone resin PVP-CL (Aldrich Chemie GmbH & Co., KG, West Germany), the polyamide resin PA 400 (M. Woelm AG, West Germany); and carbon.

In the case of polystyrene or acrylic resin a preferred eluent is a polar solvent mixture of water-miscible solvents such as those reported above; in the case of a polyamide resin the eluent is preferably an aqueous mixture of a water-miscible solvent, such as the ones mentioned above, while for carbon a preferred eluent is a lower ketone such as acetone or a lower alcohol such as methanol.

The further purification of a crude preparation of antibiotic GE 2270 can be accomplished by any of the known techniques but is preferably conducted by means of chromatographic procedures.

Examples of these chromatographic procedures are those reported above in relation to the recovery step and include also chromatography on stationary phases such as silica gel, allumina, Florisil and the like, with an organic eluting phase made of mixtures of solvents including halogenated hydrocarbons, ethers, higher ketones of the type already mentioned above or reverse-phase chromatography on silanized silica gel having various functional derivatizations and eluting with an aqueous mixture of water-miscible solvents of the kind mentioned above.

Conveniently, also the so-called steric exclusion chromatographic technique can be employed with good purification results. In particular, controlled pore cross-linked dextrans in which most hydroxyl groups have been alkylated, e.g. Sephadex LH-20 (Pharmacia Fine Chemicals, Ab), are usefully employed in this technique.

As usual in this art, the production as well as the recovery and purification steps may be monitored by a variety of analytical procedures including bioassays such as paper disc or agar diffusion assays on sensible microorganisms or TLC or HPLC procedures, which may involve a UV or microbial detention step.

A preferred HPLC technique is represented by a reverse-phase HPLC using a column with porous and spheric particles of silanized silica gel, e.g. silica gel functionalized with C-18 alkyl groups having a uniform diameter (such as 5 micrometer Ultrasphere ODS Altex; Beckman Co.), a pre-column which is a silica gel functionalized with C-18 alkyl groups (such as RP 18 Brownlee Labs) and an eluent which is a linear gradient mixture of a polar water miscible solvent, such as one of those described above, in an aqueous buffered solution. Preferably this solution is adjusted to pH 5–7. A most preferred eluent is represented by a linear gradient from 45 to 70% of eluent A in eluent B wherein eluent B is a mixture of acetonitrile/aqueous buffer, pH 5–7, 10:90 and eluent A is a mixture of acetonitrile/aqueous buffer, pH 5–7, 70:30.

Physico-chemical characteristics of antibiotic GE 2270 factor A:

A) ultraviolet absorption spectrum, which is shown in FIG. 1 of the accompanying drawings, and exhibits the following absorption maxima:

|  | $E_{1\ cm}^{1\%}$ | Lambda max (nm) |
|---|---|---|
| 0.1 M HCl |  | 245 (shoulder) |
|  |  | 310 |
| 0.1 M KOH |  | 245 (shoulder) |

-continued

|  | $E_{1\ cm}^{1\%}$ | Lambda max (nm) |
|---|---|---|
|  |  | 313 |
| Phosphate buffer pH 7.4 |  | 245 (shoulder) |
|  |  | 314 |
| Methanol |  | 244 (shoulder) |
|  | 265 | 310 |

B) infrared absorption spectrum in nujol mull which is shown in FIG. 2 of the accompanying drawings and exhibits the following absorption maxima (cm$^{-1}$): 3700–3060; 3060–2660 (nujol); 1650; 1590–1490; 1490–1420 (nujol); 1375 (nujol); 1310; 1245; 1210; 1165; 1090; 1060; 1020; 970; 930; 840, 810, 750, 720 (nujol), 700; The main functional I.R. absorption bands of this spectrum can be attributed as:

| $\nu$, (cm$^{-1}$) | Assignment |
|---|---|
| 3600–3100 | $\nu$NH, $\nu$OH |
| 1650 | amide I ($\nu$C=O) |
| 1545 | heterocyclic $\nu$C=C and $\nu$C=N |
| 1525, 1495 | amide II ($\delta$NH) |
| 1250, 1205 | aromatic $\delta$CH |
| 870 | heterocyclic $\gamma$CH |
| 745, 700 | aromatic $\gamma$CH |

$^1$H-NMR spectrum which is shown in FIG. 3 and exhibits the following groups of signals (in ppm) at 500 MHz recorded in DMSO-d$_6$ (hexadeuterodimethylsulfoxide) using TMS as the internal standard (0.00 ppm); the number of protons for each signal is reported between parenthesis: 9.02 (1); 8.68 (1); 8.70 (1); 8.57 (1); 8.50 (1); 8.43 (1); 8.37 (1); 8.26 (1); 8.25 (1); 7.4–7.20 (9); 6.96 (2); 6.02 (1); 5.30–5.18 (3); 5.01 (1); 4.97 (2); 4.80 (1); 4.56 (1); 4.30 (1); 4.26 (1); 3.98 (1); 3.81 (1); 3.79 (1); 3.38 (3); 2.72 (1); 2.58 (3); 2.48 (3); 2.16 (1); 2.13 (1); 1.96 (2); 1.88 (1); 1.34 (1); 0.87 (3); 0.84 (3);

D) $^{13}$C-NMR spectrum which is reported in FIG. 4 of the accompanying drawings exhibiting the following groups of signals (ppm) at 125 MHz in DMSO-d$_6$ with TMS as the internal reference (0.00 ppm), Q means quaternary carbon atoms or C=O groups; 173.69, Q; 171.10, Q; 169.83, Q; 169.51, Q; 168.45, Q; 168.26, Q; 167.84, Q; 165.68, Q; 164.75, Q; 161.40, Q; 161.23, Q; 160.46, Q; 160.29, Q; 159.35, Q; 153.42, Q; 150.31, Q; 150.11, Q; 149.41, Q; 146.93, Q; 144.73, Q; 143.75, Q; 142.10, Q; 141.78, Q; 141.33, CH; 140.97, Q; 139.53, Q; 128.68, CH; 127.99, 2[CH]; 127.67, Q; 127.67, CH; 126.88, CH; 126.76, 2/[CH]; 123.17, CH; 118.66, CH; 116.42, CH; 73.81, CH; 69.41, CH$_2$; 67.97, CH; 67.36, CH$_2$; 60.12, CH; 58.63, CH$_3$; 58.24, CH; 55.41, CH; 48.15, CH; 47.03, CH$_2$; 41.19, CH$_2$; 37.60, CH$_2$; 34.06, CH; 29.76, CH$_2$; 25.85, CH$_3$; 24.28, CH$_2$; 18.49, CH$_3$; 17.98, CH$_3$; 11.99, CH$_3$;

E) retention-time (R$_t$) of 14.9 min when analyzed by reverse phase HPLC under the following conditions:
 column: Ultrasphere ODS (reverse phase silanized silica gel; 5 micrometer) Altex (Beckman) 4.6 mm (i.d.)×250 mm
 pre-column: Brownlee Labs RP 18 (octadecylsilane silica gel; 5 micrometer)
 eluent A: acetonitrile:18 mM sodium phosphate 70:30 (v/v), adjusted to pH 7.0
 eluent B: acetonitrile:18 mM sodium phosphate 10:90 (v/v), adjusted to pH 7.0 elution mode: linear gradient of eluent A in eluent B from 45% to 70% in 20 min
flow rate: 1.8 ml/min
U.V. detector: 254 nm
internal standard: Chloramphenicol ($R_t$=3.7 min)

F) elemental analysis, after the sample has been previously dried at about 140° C. under inert atmosphere, which indicates the following composition: carbon, hydrogen, nitrogen, sulfur;

G) $R_f$ value of 0.37 in the following chromatographic system: dichloromethane:methanol, 9:1 (v/v) using silica gel plates (silica gel 60$F_{254}$, Merck Co) Visualization: U.V. light at 254 nm, yellow spot with iodine vapors or bioautography using *B. subtilis* ATCC 6633 on minimal Davis medium; internal standard: chloramphenicol (Rf 0.56)

H) FAB-MS analysis showing the lowest mass isotope of the protonated molecular ion at m/z 1290.3±0.1 dalton. All other peaks above 800 m/z mass units (not counting isotope peaks) in the spectrum were lower than 20% of the molecular ion, upon analysis with a Kratos MS-50 double focusing mass spectrometer under the following experimental conditions: Xe fast atom bombardment at 6 Kv; glycerol matrix; positive ionization mode I) an aminoacid analysis of the hydrochloric hydrolysate showing the presence of the following natural aminoacids: glycine, (L)proline and (L)serine, under the following experimental conditions:

the sample is hydrolyzed at 105° C. for 20 hours in the presence of 6N HCl containing 1% phenol and then derivatized in two steps as follows:

a) formation of the n-propyl esters of the carboxylic acid functions with 2M HCl in anhydrous pronapol (90° C., 1 h), and followed by drying under nitrogen;

b) conversion of the free amino groups to amides with pentafluoropropionic anhydride/anhydrous dichloromethane, 1/9 (v/v) at room temperature for 1 h followed by drying under nitrogen; the derivatized residue so obtained is dissolved in dichloromethane and analyzed by GC-MS using a HP5985B system under the following conditions: column: chiral n-propionyl-L-valine t-butylamide polysiloxane coated fused silica capillary column (25 m×0.2 mm i.d.; C.G.C. ANALYTIC); temperature program 80° C. for 4 min, then 4° C./min L) Ionization studies No ionizable functions are detected by titration with 0.1N HCl and 0.1N NaOH in Methylcellosolve/water; a weak basic function is revealed by titration with 0.1N $HClO_4$ in a non-aqueous medium (acetic acid);

M) Specific rotation $[alpha]_D^{20}$ = +140.8; absolute ethanol, at a concentration of about 5 gr/l.

The antimicrobial activity of the compounds of the invention can be demonstrated by a series of standard tests in vitro.

MIC for *Clostridium difficile*, *Propionibacterium acnes*, and *Bacteroides fragilis* are determined by agar dilution (inocula $10^4$ CFU) MIC for other organisms are determined by microbroth dilution (inocula $10^4$ to $10^5$ CFU/ml). Inocula for *Ureaplasma urealyticum* were approximately $10^4$ color changing units/ml. Incubation times are 18-24 h, except for *N. gonorrhoeae*, *Branhamella catarrhalis*, *H. influenzae*, *C. difficile*, *P. acnes*, and *B. fragilis* (48 h). All organisms are incubated at about 37° C. except for *Candida albicans* (30° C.). *N.*

*gonorrhoeae* and *H. influenzae* are incubated in a 5% $CO_2$ atmosphere, anaerobes in an anaerobic gas mixture. Media used are: Iso-Sensitest broth (Oxoid) (Staphylococci, *Streptococcus faecalis*, *Streptococcus faecium*, *Escherichia coli*, *Pseudomonas aeruginosa*, *Proteus vulgaris*, *Klebsiella pneumoniae*); Todd-Hewitt broth (Difco) (other streptococci); GC base broth (Difco) +1% IsoVitalex BBL (*N. gonorrhoeae*); brain heart infusion broth (Difco) +1% Supplement C (Difco) (*H. influenzae*); Mueller-Hinton broth (BBL) (*Branhamella catarrhalis*); AC medium (Difco) (*C. perfringens*); Wilkins-Chalgren agar (Oxoid) (other anaerobes) (T. D. Wilkins and S. Chalgren, Antimicrob. Ag. Chemother. 10, 926, 1976); Evans and Taylor-Robinson broth (Difco), with supplements, for *U. urealyticum*; yeast nitrogen broth (Difco) (*Candida albicans*).

The minimal inhibitory concentrations (MIC, micrograms/ml) for some microorganisms are reported below in Table IV.

TABLE IV

| Strain | M.I.C. (micrograms/ml) Antibiotic GE 2270 factor A |
|---|---|
| *Staph. aureus* Tour L165 | 0.25 |
| *Staph. aureus* Tour L165 ($10^6$ cfu/ml) | 0.25 |
| *Staph. aureus* Tour L165 + 30% bovine serum | 0.25 |
| *Staph. epidermidis* L147 ATCC 12228 | 0.13 |
| *Staph. haemolyticus* L602 | 0.5 |
| *Staph. haemolyticus* L602 ($10^6$ cfu/ml) | 1 |
| *Strep. pyogenes* C203 | 0.25 |
| *Strep. pneumoniae* UC41 | 0.13 |
| *Strep. faecalis* ATCC 7080 | 0.13 |
| *Strep. mitis* L796 | 0.13 |
| *Clostridium perfringens* ISS 30543 | 0.03 |
| *Clostridium difficile* ATCC 9689 | 0.03 |
| *Propionibacterium acnes* ATCC 6919 | ≦0.004 |
| *Bacteroides fragilis* ATCC 23745 | 2 |
| *Neisseria gonorrhoeae* ISM68/126 | 32 |
| *Branhamella catarrhalis* ATCC 8176 | 1 |
| *Haemophilus influenzae* ATCC 19418 | 128 |
| *Ureaplasma urealyticum* L 1479 | 32 |
| *Escherichia coli* SKF 12140 | >128 |
| *Proteus vulgaris* ATCC 881 | >128 |
| *Pseudomonas aeruginosa* ATCC 10145 | >128 |
| *Klebsiella pneumoniae* L142 | >128 |
| *Candida albicans* SKF 2270 | >128 |

The activity of antibiotic GE 2270 was also confirmed in experiments in vitro against clinical isolates of Enterococci.

Table V reports the results of these experiments.

TABLE V

| Activity of antibiotic GE 2270 against Enterococci | | | | |
|---|---|---|---|---|
| | No. of | microgram/ml | | |
| Species | strains | MIC range | $MIC_{50}$ | $MIC_{90}$ |
| *Strep. faecalis* | 15* | 0.03-0.25 | 0.06 | 0.25 |
| *Strep. faecium* | 15* | 0.06-0.5 | 0.06 | 0.13 |

*including 4 vancomycin resistant strains
*including 5 vancomycin resistant strains The results relating to some in vitro tests against clinically-isolated coagulase-negative Spaphylococci are reported below in Table VI.

TABLE VI

| Activity of antibiotic GE 2270 against coagulase-negative Staphylococci | | |
|---|---|---|
| | | MIC (microgram/ml) GE 2270 |
| *Staph. epidermidis* | L408 | 0.5 |
| | L423 | 0.25 |

TABLE VI-continued

Activity of antibiotic GE 2270 against coaugalase-negative Staphylococci

| | | MIC (microgram/ml) GE 2270 |
|---|---|---|
| | L410 | 0.5 |
| | L393 | 0.5 |
| | L425 | 0.25 |
| Staph. haemolyticus | L353 | 0.25 |
| | L602 | 1 |
| | L383 | 0.5 |
| | L626 | 0.5 |
| | L382 | 1 |
| | L620 | 1 |
| | L381 | 0.5 |

The antimicrobial spectrum of activity of antibiotic GE 2270 includes also anaerobes, as is shown by the results of the in vitro experiment reported in Table VII below.

TABLE VII

Activity of GE 2270 against Anaerobes

| | | MIC (microgram/ml) GE 2270 |
|---|---|---|
| Bacteroides fragilis | L1236 | 2 |
| | L1237 | 1 |
| | L1226 | 1 |
| | L1228 | 1 |
| | L1010 | 2 |
| Propionibacterium acnes | L1014 | 0.004 |
| | L1560 | 0.004 |
| | L1563 | 0.03 |
| | L1565 | 0.008 |

The activity against P. acnes was also confirmed in an in vitro experiment involving 11 clinically-isolated strains, whose results are reported below.

Activity of antibiotic GE 2270 against P. acnes

| No. of strains | microgram/ml | | |
|---|---|---|---|
| | MIC range | $MIC_{50}$ | $MIC_{90}$ |
| 11 | 0.004–0.008 | 0.008 | 0.008 |

Bactericidal activity against Enterococcus faecalis

Time-kill curves were run in 10 ml of Todd-Hewitt broth in 100 ml Erlenmeyer flasks, incubated at 37° C. without agitation. A logarithmically growing culture of Enterococcus faecalis strain L 149 was inoculated at $1.4 \times 10^7$ CFU/ml.

The reference antibiotic (teicoplanin, 8 mg/l) killed 99% of the infecting bacteria in 48 h, while antibiotic GE 2270 factor A (0.13 mg/l) killed 99.8% of the bacteria within 2 h and 99.99% within 48 h at this dose or within 24 h at 4 mg/l.

This activity against Enterococcus faecalis extends also to strains which are resistant to glycopeptidic antibiotics.

Activity against Gardnerella vaginalis

13 Clincial Isolates of G. vaginalis were tested on Casman agar with 5% rabbit blood and 0.15% lysed rabbit blood (inoculum approximately $10^4$ CFU) The MIC of antibiotic GE 2270 factor A was in the range 2–4 mg/l; the was 2 mg/l. The incubation was for 48 h at 37° C. in an anaerobic gas mixture.

Experimental septicemia in mice

The antimicrobial activity of the compound of the invention is confirmed also in experimental septicemia in mice.

Groups of eight CD1 mice of both sexes (Charles River, average weight 18–22 g) were infected intraperitoneally with Staphylococcus aureus ATCC 19636. The antibacterial challenge ($10^6$ cells/mouse) was given suspended in 0.5 ml of 5% bacteriological mucin (Difco). The test compound was administered intraveneously once immediately after infection in a sterile aqueous solution containing 5% dimethylformamide and 10% Cremophor $^R$EL (polyethoxylated castor oil).

The $ED_{50}$ was calculated on the seventh day from the percentage of surviving animals at each dose by the Spearman and Kaerber method; its value resulted 1.13 mg/kg.

Experimental endocarditis in rats

Endocarditis was induced in male CD rats (Charles River) weighing about 200 g. A polyethylene catheter (PP.25 Portex) was inserted through the aortic valve into the left ventricle via the right carotid artery and secured with a silk ligature. Correct positioning of the catheter was controlled using a recording amplifier (Hewlett Packard model 7782A) with a pressure transducer. Two days later, rats were infected by i.v. injection of 0.5 ml of saline containing $10^4$ CFU of S. aureus L 1524. Treatment was for 5 days starting 16 h after infection. Antibiotic GE 2270 factor A solubilized in propyleneglycol:Cremophor EL:5% glucose (10:20:70), was administered i.v. 20 mg/kg twice a day. Surviving rats were killed on the sixth day from treatment and their hearts were removed. Any animal dying before the end of the therapy was autopsied and its heart removed. Each heart was weighed and homogenized; homogenates were serially diluted and plated on Todd-Hewitt agar to determine the bacterial load. The presence of blood in the whole heart homogenates did not influence the results, as bacterial titres in the blood were always at least 1000-fold lower than heart loads. Data were statistically analysed by means of Scheffe's multiple comparison test. Those rats which died within 40 h after infection were excluded from the statistical analysis. The results of this experiment are reported below:

Activity of antiobiotic GE 2270 factor A in staphylococcal endocarditis in rats.

| Infecting organism** | Theraphy | Daily dose (mg/kg) route | No. of rats | $Log_{10}$ CFU/g heart (mean ± SD)*** |
|---|---|---|---|---|
| S. aureus L1524 | none | | 11 | 9.48 ± 0.33 |
| | vehicle | i.v. | 13 | 9.61 ± 0.31 |
| | GE 2270 factor A | (20 × 2) i.v. | 12 | 4.89 ± 1.29* |

*p < 0.001 versus controls (untreated or treated with the vehicle)
**MIC of antibiotic GE 2270 factor A for S. aureus L1524: 0.25 microgram/ml.

Acute toxicity

Acute toxicity tests carried out in mice revealed that the $LD_{50}$ for antiobiotic GE 2270 factor A was higher than 100 mg/kg i.v. and higher than 500 mg/kg i.p. in that animal species.

In view of its properties, the compound of the invention can be used as active ingredient in the preparation of medicaments for human or animal treatment.

In particular, antibiotic GE 2270 factor A is an antimicrobial agent mainly active against gram positive bacteria and gram positive as well as gram negative anaerobes. It appears to be very active also in Staphylococcal endocarditis without any cross-resistance with meticillin, aminoglycosides or glycopeptide antibiotics.

The main therapeutic indication of the antibiotic substance of the invention is thus in the treatment of infections related to the presence of a microorganism susceptible to it.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixture with pharmaceutically acceptable carriers and can also be administered in conjunction with other antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

A preferred pharmaceutical formulation is represented by a formulation suitable for a topical application on an intact or damaged skin or mucous membrane. Examples of such formulations are powders, ointments, creams and lotions. The excipients in these formulations are the usual pharmaceutically acceptable vehicles such as oleaginous ointment bases (e.g. cetyl esters wax, oleic acid, olive oil, paraffin, spermaceti, starch glycerite); absorbent ointment bases (e.g. anhydrous lanolin, hydrophilic petrolatum), emulsion ointment bases (e.g. cetyl alcohol, glyceryl monostearate, lanolin, stearic acid), water-soluble ointment bases (e.g. glycol ethers and their derivatives which include polyethylene glycols, poly(oxy-1,2-ethanediyl)-alpha-hydro-omega-hydroxy-octadecanoate, polysorbates, and polyethylene glycols mono-stearates).

These formulations may contain other known excipients, such as preservatives and are prepared as known in the art and reported in reference handbooks such as Remington's Pharmaceutical Sciences, Seventeenth edition, 1985, Mack Publishing Co.

The compounds of the invention can also be formulated into formulations suitable for parenteral administration according to precedures known per se in the art and reported in reference books such as the one mentioned above.

For instance, a compound of the invention is formulated with a solubilizing agent such as polypropylene glycol or dimethylacetamide and a surface-active agent such as polyoxyethylene sorbitan mono-oleate or polyethoxylated castor oil in steril water for injection.

An example of a typical formulation for parenteral administration contains 10 mg of antibiotic GE 2270 factor A for ml of final preparation, 10-20% of a surface-active agent which may be a polyoxyethylene sorbitan fatty acid ester, a polyoxyethylene castor oil derivative or a polyoxyethylene hydrogenated castor oil derivative and 0-20%, and preferably 10-20% of a solubilizing agent such as propylene glycol, dimethylacetamide, dimethylformamide, ter-butyl-N-hydroxycarmabate, 1,2-, 1,3-, or 1,4-butanediol, ethyl oleate, tetrahydrofurfuryl-polyethylene-glycol 200, dimethyl isosorbide, benzyl alcohol and the like. A preferred solubilizing agent is propylene glycol.

Polyoxyethylene sorbitan fatty acid esters are commercially available and some of them are traded under the trade name "Tween". They are also known with the non-proprietary name of "polysorbates". Examples of them are polysorbate 20, 21, 40, 60, 61, 65, 80, 81 and 85. Preferred for use in the formulations of the invention is polysorbate 80 (sorbitan mono-9-octadecanoate, poly-(oxy-1,2-ethanediyl)derivatives).

Polyoxyethylene castor oils and polyoxyethylene hydrogenated castor oils are also commercially available. Some of them are traded with the trade name "Cremóphor". Examples of such compounds are those known as Cremophor EL (polyethoxylated castor oil), Cremophor RH 40 (polyethoxylated hydrogenated castor oil), Cremophor RH 60 (PEG 60 hydrogenated castor oil) or Emulphor EL-719 (polyoxyethylated vegetable oil).

Preferably, a formulation for injection should have a pH in the range of 7±0.5. If necessary, it might be advisable to adjust the pH of the preparation with a suitable buffering agent. Conveniently, TRIS (i.e. trihydroxymethylaminomethane) or phosphate can be used as buffering agents.

A preferred formulation for parenteral administration includes the following excipients: Cremophor $^R$ EL (polyoxyl 35 castor oil USP/NF) 20%, propylene glycol from 5 to 20%, preferably 10-20%.

Generally, these formulations can be prepared by dissolving the active ingredient into the organic solvent, then adding, with sitting, the surface active ingredient, and finally diluting to the desired volume with sterile water for injection.

Other excipients, such as preservative or stabilizing agents can be added as known in the art.

An example of a parenteral formulation is the following:

| | |
|---|---|
| antibiotic GE 2270 factor A | 10 mg |
| PEG 40 castor oil (Cremophor EL) | 0.2 ml |
| propylene glycol | 0.2 ml |
| methyl parahydroxybenzoate | 0.5 mg |
| propyl parahydroxybenzoate | 0.05 mg |
| water for injection q.s. | 1 ml |

Alternatively, the active ingredient may be prepared as a lyophilized powder for reconstitution before use.

If the lyophilized material is prepared starting from a mixture containing the active ingredient and the surfactant, such as polyethylene glycol 60 hydrogenated castor oil, it can conveniently be reconstituted with the aqueous medium alone, without addition of an organic solvent.

Optionally, a common lyophilization aid can be added, if necessary, to obtain a lyophilized material in powder form.

Preferably, all these formulations are used for i.v. administration in the treatment of any infection involving a microorganism susceptible to the antibiotic of the invention.

In the treatment of pseudomembranous colitis or other diseases attributable to the presence of anaerobes in the gastrointestinal tract, an effective dose of the compound of the invention may be administered orally in a suitable pharmaceutical form such as a capsule, a tablet or an aqueous suspension.

The dosage of the active ingredient depends on many factors which include type, age and conditions of the patient, specific active ingredient and formulation selected for the administration, administration schedule, etc.

In general, effective antimicrobial dosages are employed per single unit dosage form.

Repeated applications/administrations, e.g. from 2 to 6 times a day, are in general preferred. An effective dosage may be in general in the range 0.5-50 mg/kg body weight/day.

A preferred topic preparation is an ointment containing from 1% to 10% of a compound of the present invention.

Anyway, the prescribing physician will be able to determine the optimal dosage for a given patient in a given situation.

Besides their use as medicaments in human and veterinary therapy, the compounds of the invention can also be used as animal growth promoters.

For this purpose, a compound of the invention is administered orally in a suitable feed. The exact concentration employed is that which is required to provide for the active agent in a growth promotant effective amount when normal amounts of feed are consumed.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and CO., S. Francisco, USA, 1969 or "Livestock Feeds and Feeding" O and B books, Corvallis, Oregon, USA, 1977).

Figure 1:
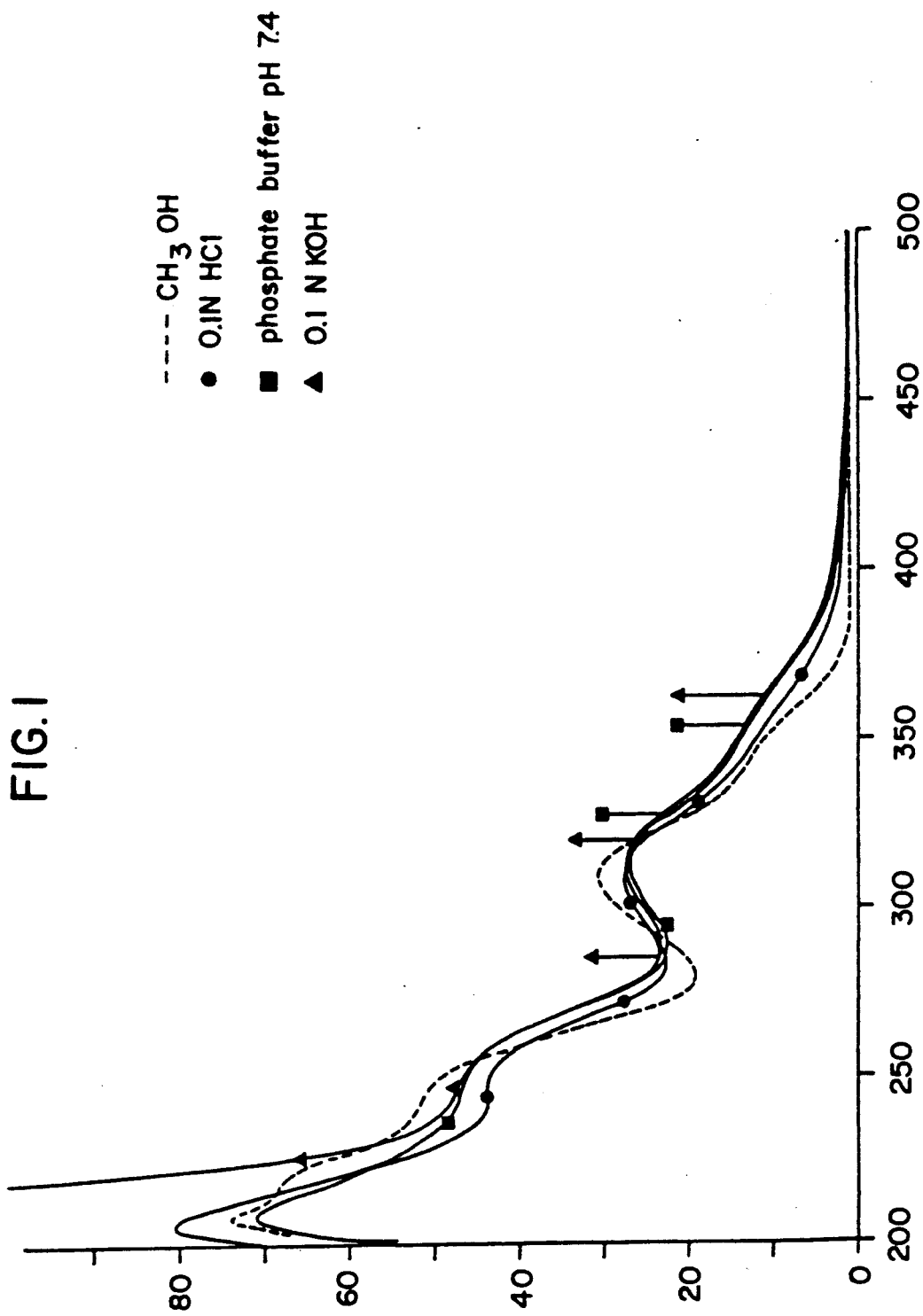
FIG. 1 reports the UV spectrum of antibiotic GE 2270 factor A. The correspondence between the symbols and the employed solvents is the following:
- - - - refers to the assay in $CH_3OH$
● refers to the assay in $0.1N$ HCl
■ refers to the assay in phosphate buffer pH 7.4
▲ refers to the assay in $0.1N$ KOH
Figure 2:
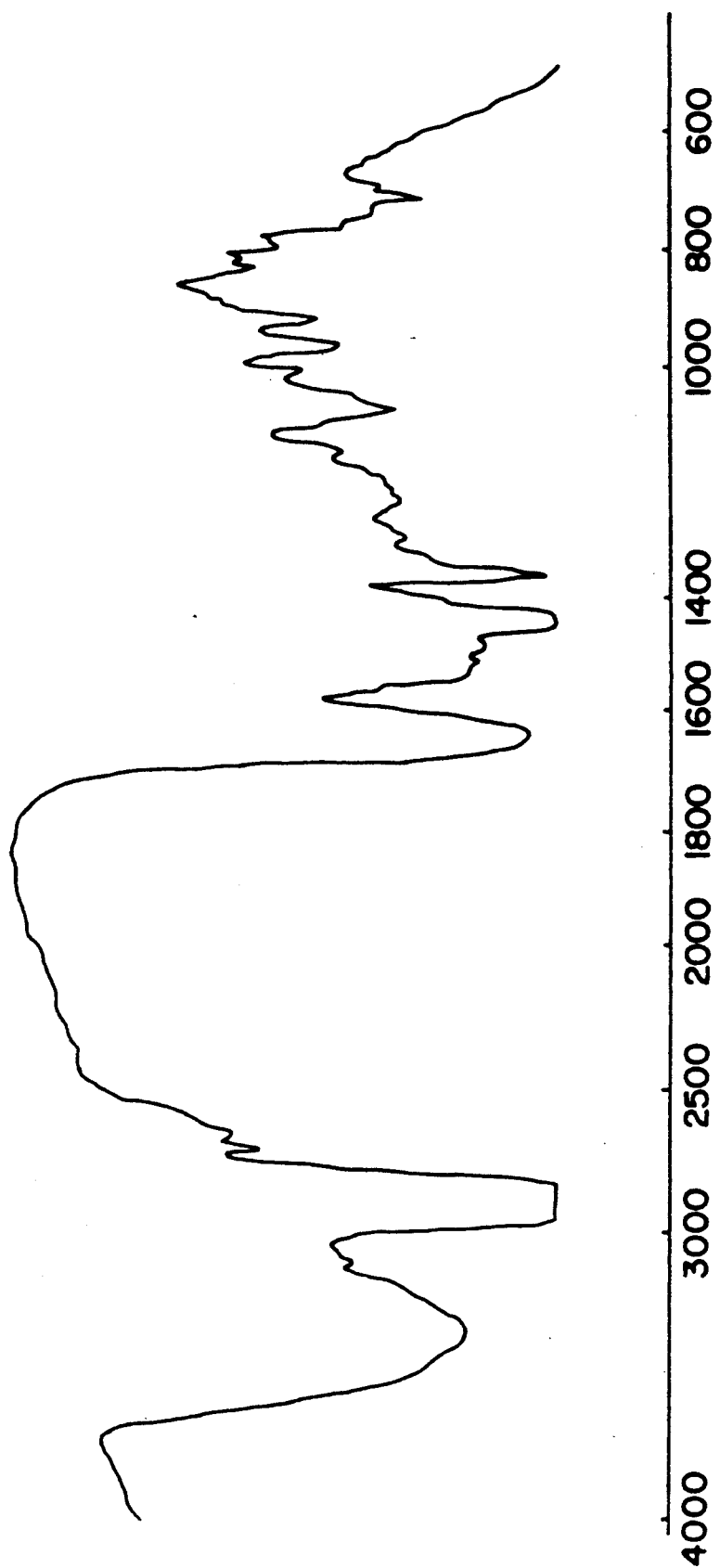
FIG. 2 represents the I.R. absorption spectrum of antibiotic GE 2270 factor A in nujol mull

The following examples further illustrate the invention and have not to be interpreted as limiting it in any way.

EXAMPLE 1

Production of antibiotic GE 2270

A culture of *Planobispora rosea* ATCC 53773 is grown on an oatmeal agar slant for two weeks at 28°-30° C. and then used to inoculate 500 ml flasks containing 100 ml of a seed medium of the following composition:

| Starch | 20 g/l |
| Polypeptone | 5 g/l |
| Yeast extract | 3 g/l |
| Beef extract | 2 g/l |
| Soybean meal | 2 g/l |
| Calcium carbonate | 1 g/l |
| Distilled water q.s. | 100 ml |

(adjusted to pH 7.0 before sterilization)

The flask is incubated on a rotary shaker (200 rpm at 28°-30° C. for 92 h. The obtained culture is then used to inoculate a jar fermenter containing 4 liters of the same medium and the culture is incubated at 28°-30° C. for hours with stirring (about 900 rpm) and aeration (about one standard liter of air per volume per minute).

The obtained broth is transferred to a fermenter containing 50 l of the following production medium:

| Starch | 20 g/l |
| Peptone | 2.5 g/l |
| Hydrolyzed casein | 2.5 g/l |
| Yeast extract | 3 g/l |
| Beef extract | 2 g/l |
| Soybean meal | 2 g/l |
| Calcium carbonate | 1 g/l |
| Distilled water | q.s. |

(adjusted to pH 7.0 before sterilization)

and incubated for about 72 hours at 28°-30° C.

Antibiotic production is monitored by paper disc agar assay using *B. subtilis* ATCC 6633 grown on minimum Davis medium. The inhibition zones are evaluated after incubation overnight at 35° C.

EXAMPLE 2

Recovery of antibiotic GE 2270

The fermentation mass (50 l) obtained above is harvested and submitted to filtration in the presence of a filter aid (Clarcell).

Antibiotic GE 2270 is found mainly in the mycelium, even if a certain amount of it can be recovered also from the filtrates.

a) The filtrate is adjusted to about pH 7.0 and extracted with ethyl acetate (50 l). The organic phase is separated by centrifugation and concentrated to a small volume under reduced pressure. The obtained oily residue is then treated with petroleum ether to precipitate crude antibiotic GE 2270 that is collected by filtration and dried. 415 mg of crude antibiotic GE 2270 complex is obtained.

b) The mycelium is extracted twice with 20 l of methanol and the pooled extracts are concentrated under reduced pressure to give an aqueous residue which is extracted twice with ethyl acetate. Crude antibiotic GE 2270 (6.06 g) is precipitated by addition of petroleum ether from the concentrated organic phase.

EXAMPLE 3

Purification of antibiotic GE 2270 factor A

The crude obtained from the mycelium according to the procedure described above (3 g) is dissolved in tetrahydrofuran and concentrated under reduced pressure in the presence of silica gel (230-400 mesh). The obtained solid residue is collected and applied to a chromatography column containing 300 g of silica gel (230-400 mesh) prepared in methylene chloride ($CH_2Cl_2$). The column is developed first with methylene chloride (2 l) and then sequentially with 1.5 l mixtures of methylene chloride and methanol in the following ratios: 98/2; 96/4, 94/6, 92/8, 90/10 and 88/12 (v/v).

Fractions are collected, analyzed by TLC, HPLC or microbiologically against *B. subtilis* and pooled according to their antibiotic content.

The pooled fractions containing pure antibiotic GE 2270 factor A (HPLC retention time 14.9 min, see the physico-chemical data, point E, above) are concentrated under reduced pressure to give an oily residue which is solubilized with tetrahydrofuran. From this solution, antibiotic GE 2270 factor A (600 mg) is precipitated by adding petroleum ether.

EXAMPLE 4

Another crop of antibiotic GE 2270 factor A is obtained from other fractions separated by the above described chromatographic system but which contain it in an impure form (HPLC). Also these fractions are pooled, concentrated and treated to obtain a solid as described above. This crude preparation of antibiotic GE 2270 factor A is purified by HPLC according to the following procedure:

A portion of this precipitate (6 mg) is dissolved in acetonitrile:water, 1:1 (v/v) and injected into a HPLC chromatographic system equipped with a silanized silica gel column (Lichrosorb RP 18, 7 micrometer, 250×10 mm, Merck, Darmstadt).

Elution is made with a linear gradient of a mixture of solution A and B from 50% to 85% of A in B, in 20 min, at a flow rate of about 4 ml/min. Solution A is a mixture of acetonitrile and 18 mM sodium phosphate buffer 70/30 (v/v), adjusted to pH 6, while solution B is a mixture of acetonitrile and 18 mM phosphate buffer, 10/90 (v/v), adjusted to pH 6.

The column is connected to a Perkin Elmer LC85 UV detector at 330 nm. The fractions of 11 subsequent chromatographic runs having homogeneous content are pooled and concentrated under reduced pressure to remove acetonitrile thus obtaining separated residual solutions containing antibiotic GE 2270 factor A. These solutions are extracted twice with an equal volume of ethyl acetate and the antibiotic product is obtained by precipitation from the concentrated organic phase by adding petroleum ether. Upon recovery by filtration and drying, 27 mg of antibiotic GE 2270 factor A are obtained.

We claim:

1. A process for preparing Antibiotic GE 2270 factor A having the following characteristics, in the non-salt form:

A) ultraviolet absorption spectrum, which exhibits the following absorption maxima:

|  | $E_{1\ cm}^{1\%}$ | Lambda max (nm) |
|---|---|---|
| 0.1 M HCl |  | 245 (shoulder) |
|  |  | 310 |
| 0.1 M KOH |  | 245 (shoulder) |
|  |  | 313 |
| Phosphate buffer pH 7.4 |  | 245 (shoulder) |
|  |  | 314 |
| Methanol |  | 244 (shoulder) |
|  | 265 | 310 |

B) infrared absorption spectrum in nujol mull which exhibits the following absorption maxima (cm$^{-1}$): 3700–3060; 3060–2660 (nujol); 1650; 1590–1490; 1490–1420 (nujol); 1375 (nujol); 1310; 1245; 1210; 1165; 1090; 1060; 1020; 970; 930; 840, 810, 750, 720 (nujol), 700;

The main functional I.R. absorption bands of this spectrum can be attributed as:

| $\nu$, (cm$^{-1}$) | Assignment |
|---|---|
| 3600–3100 | $\nu$NH, $\nu$OH |
| 1650 | amide I ($\nu$C=O) |
| 1545 | heterocyclic $\nu$C=C and $\nu$C=N |
| 1525, 1495 | amide II ($\delta$NH) |
| 1250, 1205 | aromatic $\delta$CH |
| 870 | heterocyclic $\gamma$CH |
| 745, 700 | aromatic $\gamma$CH |

Figure 3:
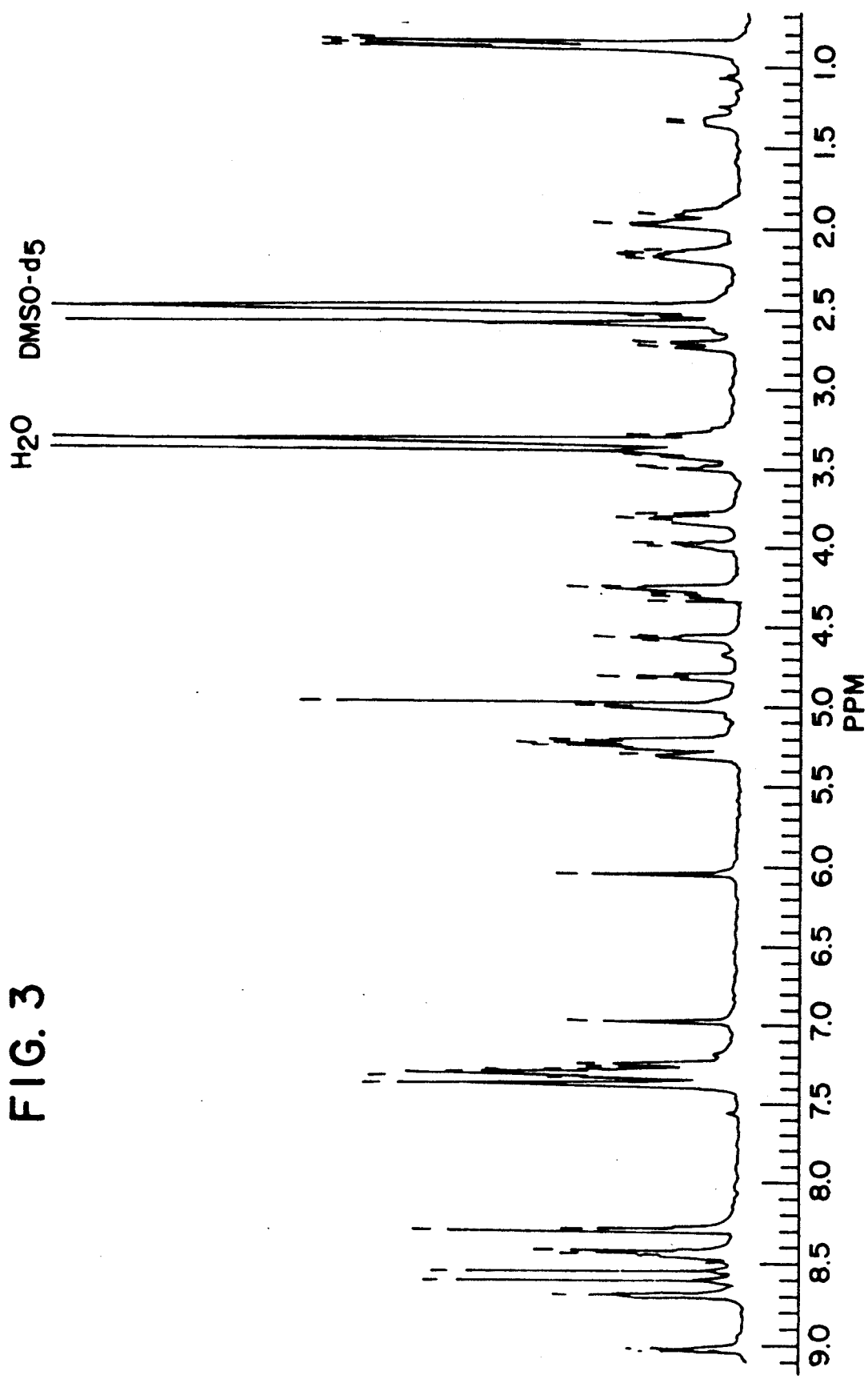
FIG. 3 represents the $^1$H-NMR of antibiotic GE 2270 factor A measured at 500 MHz in DMSO-$d_6$.
Figure 4:
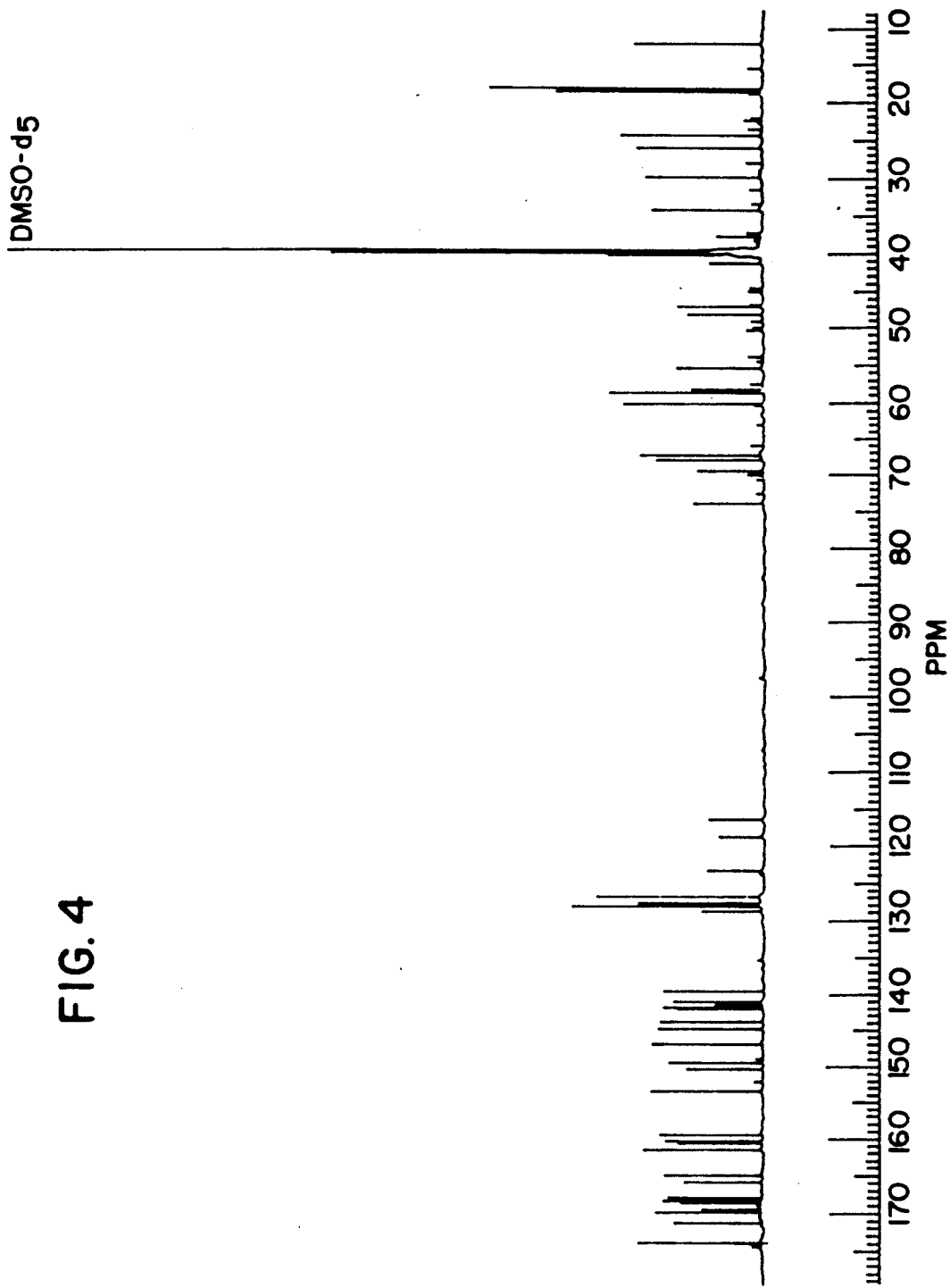
FIG. 4 represents the $^{13}$C-NMR of antibiotic GE 2270 factor A at 125 MHz in DMSO-$d_6$.

$^1$H-NMR spectrum which is shown in FIG. 3 and exhibits the following groups of signals (in ppm) at 500 MHz recorded in DMSO-d$_6$ (hexadeuterodimethylsulfoxide) using TMS as the internal standard (0.00 ppm); the number of protons for each signal is reported between parenthesis: 9.02 (1); 8.68 (1); 8.70 (1); 8.57 (1); 8.50 (1); 8.43 (1); 8.37 (1); 8.26 (1); 8.25 (1); 7.4–7.20 (9); 6.96 (2); 6.02 (1); 5.30–5.18 (3); 5.01 (1); 4.97 (2); 4.80 (1); 4.56 (1); 4.30 (1); 4.26 (1); 3.98 (1); 3.81 (1); 3.79 (1); 3.38 (3); 2.72 (1); 2.58 (3); 2.48 (3); 2.16 (1); 2.13 (1); 1.96 (2); 1.88 (1); 1.34 (1); 0.87 (3); 0.84 (3);

D) $^{13}$C-NMR spectrum which is reported in FIG. 4 of the accompanying drawings exhibiting the following groups of signals (ppm) at 125 MHz in DMSO-d$_6$ with TMS as the internal reference (0.00 ppm), Q means quaternary carbon atoms or C=O groups;
173.69, Q; 171.10, Q; 169.83, Q; 169.51, Q; 168.45, Q; 168.26, Q; 167.84, Q; 165.68, Q; 164.75, Q; 161.40, Q; 161.23, Q; 160.46, Q; 160.29, Q; 159.35, Q; 153.42, Q; 150.31, Q; 150.11, Q; 149.41, Q; 146.93, Q; 144.73, Q; 143.75, Q; 142.10, Q; 141.78, Q; 141.33, CH; 140.97, Q; 139.53, Q; 128.68, CH; 127.99, 2[CH]; 127.67, Q; 127.67, CH; 126.88, CH; 126.76, 2/[CH]; 123.17, CH; 118.66, CH; 116.42, CH; 73.81, CH; 69.41, CH$_2$; 67.97, CH; 67.36, CH$_2$; 60.12, CH; 58.63, CH$_3$; 58.24, CH; 55.41, CH; 48.15, CH; 47.03, CH$_2$; 41.19, CH$_2$; 37.60, CH$_2$; 34.06, CH; 29.76, CH$_2$; 25.85, CH$_3$; 24.28, CH$_2$; 18.49, CH$_3$; 17.98, CH$_3$; 11.99, CH$_3$;

E) retention-time (R$_t$) of 14.9 min when analyzed by reverse phase HPLC under the following conditions:

column: Ultrasphere ODS (reverse phase silanized silica gel; 5 micrometer) Altex (Beckman) 4.6 mm (i.d.)×250 mm
pre-column: Brownlee Labs RP 18 (octadecylsilane silica gel; 5 micrometer)
eluent A: acetonitrile:18 mM sodium phosphate 70:30 (v/v), adjusted to pH 7.0
eluent B: acetonitrile:18 mM sodium phosphate 10:90 (v/v), adjusted to pH 7.0
elution mode: linear gradient of eluent A in eluent B from 45% to 70% in 20 min
flow rate: 1.8 ml/min
U.V. detector: 254 nm
internal standard: Chloramphenicol (R$_t$=3.7 min)

F) elemental analysis, after the sample has been previously dried at about 140° C. under inert atmosphere, which indicates the following composition: carbon, hydrogen, nitrogen, sulfur;

G) $R_f$ value of 0.37 in the following chromatographic system: dichloromethane:methanol, 9:1 (v/v) using silica gel plates (silica gel 60F$_{254}$, Merck Co) Visualization: U.V. light at 254 nm, yellow spot with iodine vapors or bioautography using *B. subtilis* ATCC 6633 on minimal Davis medium; internal standard: chloramphenicol (Rf 0.56)

H) FAB-MS analysis showing the lowest mass isotope of the protonated molecular ion at m/z 1290.3±0.1 dalton. All other peaks above 800 m/z mass units (not counting isotope peaks) in the spectrum were lower than 20% of the molecular ion, upon analysis with a Kratos MS-50 double focusing mass spectrometer under the following experimental conditions: Xe fast atom bombardment at 6 Kv; glycerol matrix; positive ionization mode I) an aminoacid analysis of the hydrochloric hydrolysate showing the presence of the following natural aminoacids: glycine, (L)proline and (L)serine, under the following experimental conditions: the sample is hydrolyzed at 105° C. for 20 hours in the presence of 6N HCl containing 1% phenol and then derivatized in two steps as follows:

a) formation of the n-propyl esters of the carboxylic acid functions with 2M HCl in anhydrous pronapol (90° C., 1 h), and followed by drying under nitrogen;

b) conversion of the free amino groups to amides with pentafluoropropionic anhydride/anhydrous dichloromethane, 1/9 (v/v) at room temperature for 1 h followed by drying under nitrogen;

the derivatized residue so obtained is dissolved in dichloromethane and analyzed by GC-MS using a HP5985B system under the following conditions: column: chiral n-propionyl-L-valine t-butylamide polysiloxane coated fused silica capillary column (25 m×0.2 mm i.d.; C.G.C. ANALYTIC); temperature program 80° C. for 4 min, then 4° C./min L) Ionization studies
No ionizable functions are detected by titration with 0.1N HCl and 0.1N NaOH in Methylcellosolve/water; a weak basic function is revealed by titration with 0.1N HClO$_4$ in a non-aqueous medium (acetic acid);

M) Specific rotation
[alpha]$_D^{20}$ = +140.8; absolute ethanol, at a concentration of about 5 gr/l, which comprises cultivating *Planobispora rosea* ATCC 53773 or a GE 2270 producing variant or mutant under submerged aerobic conditions in the presence of assimilable sources of carbon, nitrogen and inorganic salts and recovering the produced antibiotic therefrom.

2. A process according to claim 1 in which *Planobispora rosea* ATCC 53773 is cultivated.

* * * * *

UNITED STATES PATENT AND TRADEMARK OFFICE
CERTIFICATE OF CORRECTION

PATENT NO. : 5,202,241
DATED : April 13, 1993
INVENTOR(S) : E. Selva et al.

It is certified that error appears in the above-identified patent and that said Letters Patent is hereby corrected as shown below:

Column 11, line 67, "the was 2 mg/1." should read --the $MIC_{50}$ was 2 mg/1.--

Column 12, after line 61, insert --***Heart bacterial load at the onset of therapy: 7.36 ± 0.32 (mean ± SD of log 10 CFU/g of heart for 5 animals)--

Signed and Sealed this

Twenty-seventh Day of September, 1994

Attest:

BRUCE LEHMAN

Attesting Officer

Commissioner of Patents and Trademarks